(12) United States Patent
Virnig et al.

(10) Patent No.: US 7,585,475 B2
(45) Date of Patent: Sep. 8, 2009

(54) HIGHLY-CONDUCTIVE COPPER EXTRACTANT FORMULATIONS

(75) Inventors: Michael J. Virnig, Tucson, AZ (US); Daniel McSweeney, County Cork (IE); Frank McDonnell, County Cork (IE)

(73) Assignee: Cognis IP Management GmbH, Duesseldorf (DE)

( * ) Notice: Subject to any disclaimer, the term of this patent is extended or adjusted under 35 U.S.C. 154(b) by 0 days.

(21) Appl. No.: 11/827,630

(22) Filed: Jul. 12, 2007

(65) Prior Publication Data

US 2008/0035893 A1 Feb. 14, 2008

Related U.S. Application Data

(60) Provisional application No. 60/837,170, filed on Aug. 11, 2006.

(51) Int. Cl.
*B01D 11/00* (2006.01)
(52) U.S. Cl. .......................... 423/24; 252/184; 252/500; 423/23
(58) Field of Classification Search ................. 252/500, 252/184; 423/23, 24
See application file for complete search history.

(56) References Cited

U.S. PATENT DOCUMENTS

| | | | |
|---|---|---|---|
| 2,915,551 A | 12/1959 | Wolf et al. | |
| 3,637,711 A | 1/1972 | Budde, Jr. et al. | |
| 4,045,441 A | 8/1977 | Richards et al. | |
| 4,065,502 A | 12/1977 | MacKay et al. | |
| 4,066,652 A | 1/1978 | Hartlage | |
| 4,175,012 A | 11/1979 | MacKay et al. | |
| 4,507,268 A | 3/1985 | Kordosky et al. | |
| 4,978,788 A | 12/1990 | Dalton et al. | |
| 5,176,843 A | 1/1993 | Dalton et al. | |
| 5,281,336 A | 1/1994 | Dalton et al. | |
| 6,107,523 A | 8/2000 | Virnig et al. | |
| 6,113,804 A | 9/2000 | Dalton et al. | |
| 6,177,055 B1 | 1/2001 | Virnig et al. | |
| 6,210,647 B1 | 4/2001 | Virnig et al. | |
| 6,231,784 B1 | 5/2001 | Virnig et al. | |
| 6,277,300 B1 | 8/2001 | Dalton et al. | |
| 6,395,062 B2 * | 5/2002 | Olafson et al. | 75/722 |
| 7,025,899 B2 * | 4/2006 | Sudderth et al. | 252/184 |
| 7,309,474 B2 * | 12/2007 | Soderstrom | 423/24 |
| 2004/0208807 A1 | 10/2004 | Soderstrom | |
| 2005/0087722 A1 | 4/2005 | Sudderth et al. | |

OTHER PUBLICATIONS

Heam et al., "Static Electricity—A Danger Inherent in the Solvent Extraction Process", Proceedings of the ALTA Conference, (2005), pp. 1-8.
Chubb et al., "Electrostatic Safety During The Solvent Extraction Of Copper", Journal of Electrostatics, 63, (2005), pp. 119-127.
Giles et al., "The Use of Additives to Increase The Conductivity of SX Organics", ALTA 2006 Copper Conference, Perth, Australia, (May 18-19, 2006), pp. 1-13.
Sastre et al., "Discussion of the Physicochemical Effects of Modifiers on the Extraction Properties of Hydroxyoximes. A Review", Solvent Extraction and Ion Exchange, vol. 22, No. 5, (2004), pp. 737-759.
Kordosky et al, "Equilibrium Modifiers In Copper Solvent Extraction Reagents—Friend or Foe?", Proceeding of Hydromet 2003, TMS, (2003), pp. 1-13.
Haig et al., "Electrostatic Hazards In Solvent Extract Plants", ALTA 2003 SX/IX World Summit, (2003), pp. 1-17.
Katritzsky et al. "Synthesis of beta-Akoxy Ketones and alpha-Functionalized beta-Alkoxy Ketones Utilizing Benzotriazole-Stabilized Acyl Anion Synthons," In: Published Papers, University of Florida (1998), pp. 1473-1477, p. 1473 [online], [retrieved on Mar. 11, 2008]. Retrieved from the Internet: <http://ark.chem.uft.edu/Published_Papers/PDF/797.pdf>.
Resolution Performance Products, "Product Brochure: Electrostatic Hazards in Handling Epikote Resins and Preparing Resin Solutions" [online]. Oct. 2002, p. 4 [retrieved on Mar. 11, 2008]. Retrieved from the internet: <http://www.resins.com/resins/eu/pdf/ek-1-6-3.pdf>.

* cited by examiner

*Primary Examiner*—Mark Kopec
*Assistant Examiner*—Haidung D Nguyen

(57) ABSTRACT

A method of creating solvent extraction reagent formulations that have high conductivity by combining (a) phenolic oxime extraction reagent(s) or other extraction reagent(s) in the organic phase of a solvent extraction circuit of a metal recovery operation, comprising combining the phenolic oxime extraction reagent(s) or other reagent(s) with one or more ketone, nitrile and/or amide compounds, or mixtures thereof, to create an extraction reagent formulation with a conductivity of at least 4,000 pS/m, measured according to the provisions of BS 5958 Part I, as well as a method of creating an organic phase that has a high conductivity, preferably a conductivity of at least 250 pS/m, comprising adding to that organic phase in an extraction circuit a phenolic oxime extraction reagent formulation with one or more ketoxime, aldoxime, mixtures thereof, or one or more other extraction reagents, and one or more ketone, nitrile, or amide compounds, or mixture thereof, and novel ketone, nitrile and amide compounds.

11 Claims, No Drawings

HIGHLY-CONDUCTIVE COPPER EXTRACTANT FORMULATIONS

CROSS-REFERENCE TO RELATED APPLICATIONS

This application claims priority under 35 U.S.C. §119(e) from provisional U.S. Patent Application No. 60/837,170, filed on Aug. 11, 2006, the entire contents of which are incorporated herein by reference.

BACKGROUND OF THE INVENTION

Recent fires in copper solvent extraction plants have underscored the need for copper solvent extraction reagent formulations that would also provide increased electrical conductivity to the organic phase. See: "Static Electricity—A Danger Inherent in Solvent Extraction Processes", G. Hearn and P. Smithson, Proceedings of the Alta Conference 2005; and "Electrostatic safety during the solvent extraction of copper", J. N. Chubb, P. Lagos and J. Lienlaf, Journal of Electrostatics 63 (2005), pp. 119-127. As a result of such studies, it has generally been determined empirically that, in order to prevent static buildup in metal extraction circuits, a conductivity of about 250-500 pS/m, as determined by the methods of BS5958 Part I (British Standard Code of Practice for Control of Undesirable Static Electricity) is desirable in the organic phase in the solvent extraction circuit, depending on the velocity at which the organic phase is being pumped.

Since the organic phase in an extraction circuit is, generally, predominantly a kerosene mixture, with an inherently low conductivity, static electricity generated, e.g., by the organic solution flowing through non-conductive pipes or flexible hoses, circulating through partly-filled tanks, and/or in the mixing and/or settling steps in the solvent extraction and stripping stages in the circuit, is likely to build, rather than to dissipate. That buildup of static charge in the organic phase could result in a discharge that might result in a fire in the extraction circuit.

One potential solution to an electrostatic charge buildup is the addition to the organic phase of conductivity aids, such as those used in pumped hydrocarbon products, such as kerosene, or motor fuels, such as diesel fuel and jet fuel. Examples of such conductivity aids are the Octastat® products, marketed by Octel Corporation, case studies with which, for Olympic Dam Operations' copper extraction circuit, have been reported in "Additives to Increase the Conductivity of SX Organics to Reduce Static Generation", M. Giles and D. White, Alta 2006 Copper Conference, May 18-19, Perth, Australia. These Octastat products, which are mixtures of quaternary ammonium compounds with an organic anionic compound, typically a sulfonic acid, unfortunately, may have an adverse effect on the metal extraction process. Their sulfonic acids, which are strong acids, can promote the hydrolysis of the oximes, resulting in degradation of the extractant formulation, and/or they may promote physical problems in the solvent extraction circuits, such as phase separation and/or entrainment issues.

Additives for and/or modifiers of extraction and stripping equilibria are frequently incorporated in commercial solvent extraction reagent formulations, which include the so-called "strong" phenolic oxime extractants. Such extractants are capable of forming very stable complexes/chelates with copper at quite low pH's and, consequently, require the use of very highly-acidic aqueous stripping solutions in order to effect the breakdown of the copper-extractant complex. Where extreme acidity of stripping solutions could generate problems in subsequent conventional electrodeposition processes, modifiers may be incorporated in these solutions in order to shift equilibria in a manner facilitating stripping at lower acidities and to enhance overall metal extraction efficiency.

The use of such equilibrium modifiers (also known as "thermodynamic modifiers") in combination with oximes, such as the broad range of chemical classes that may be used as equilibrium modifiers in combination with, e.g., 5-nonylsalicylaldoxime (NSO), is described in U.S. Pat. No. 6,231,784 (Virnig et al), the contents of which are incorporated herein by reference. The use of such modifiers in organic solutions for extracting copper salts from aqueous acidic, particularly sulfate, solutions is well known, as is the use of equilibrium modifiers in combination with either or both aldoxime(s) or/and ketoxime(s), such as described in U.S. Pat. No. 6,210,647 B1 (Virnig et al), the contents of which are incorporated herein by reference, in organic solutions for extracting metal salts from aqueous ammoniacal solutions.

Some of these formulations incorporating a modifier include P5100, a mixture of a nonylphenol (NP) modifier in combination with NSO, introduced by ICI to the industry in the early 80's. Henkel subsequently introduced LIX®T 622 extraction reagent formulation, a mixture of isotridecyl alcohol (TDA) with 5-dodecylsalicylaldoxime, and then LIX® 622N extraction reagent formulation, a mixture of TDA in combination with NSO. U.S. Pat. Nos. 4,978,788; 5,176,843; 5,281,336; 6,113,804; and 6,277,300 (all Dalton et al), the contents of which are incorporated herein by reference, describe formulations based on the use of highly-branched alcohols and esters, such as 2,2,4-trimethyl-1,3-pentanediol di-isobutyrate (TXIB), as modifiers. And U.S. Pat. No. 6,177,055 (Virnig et al), the contents of which are incorporated herein by reference, discloses the use of linear esters, such as di-n-butyl adipate (DBA), as equilibrium modifiers for extraction reagents.

The effects of such equilibrium modifiers in extraction formulations have also been reported in "Discussion of the Physiochemical Effects of Modifiers on the Extraction Properties of Hydroxyamines. A Review", A. M. Sastre and J. Szymanowski, Solvent Extraction and Ion Exchange, Vol. 22(5), pp 737-759 (2004); and in "Equilibrium Modifiers in Copper Solvent Extraction Reagents—Friend or Foe?", G. Kordosky and M. Virnig, Proceeding of Hydromet 2003, TMS, 2003.

However, kinetic additives and/or equilibrium modifiers have not been reported as having any effect on the conductivity of the organic phase in a solvent extraction circuit. Esters, which are well-known equilibrium modifiers, appear to impart no or only a marginal increase in conductivity to the organic phase of a leaching-solvent extraction-stripping-electrowinning circuit, nor do ethers seem to offer such an advantage, suggesting that there is no direct correlation between equilibrium modification and conductivity enhancement in solvent extraction circuits—certainly not to the extent sufficient to provide a beneficial effect on the conductivity of the organic phase of a metal extraction circuit.

BRIEF SUMMARY OF THE INVENTION

A method for reducing the potential of electrostatic charge buildup and possible discharge that could result in a fire in solvent extraction circuits has now been surprisingly found that combines certain classes of ketone, nitrile and amide compounds with phenolic oxime extraction reagents to create metal extraction formulations that have high electrical conductivity. With such highly-conductive extraction reagent formulations, the need to use the known, but potentially-detrimental, conductivity aids in the organic phase in metal extraction circuits is substantially reduced or eliminated.

Thus, one aspect of the present invention provides a method of creating a phenolic oxime extraction reagent formulation having high electrical conductivity, comprising combining the desired phenolic oxime extraction reagent(s) with at least one compound having one or more ketone, nitrile and/or amide functional units, or a combination of two or more ketone, nitrile or amide compounds, enough carbon atoms (preferably, 8-to-30, more preferably, 8-to-24, and most preferably, 10-to-24) to insure solubility in the organic phase, and a high enough boiling point that they do not pose a concern with respect to the flash point (preferably above 140° F.) of the organic phase.

The present invention further provides a method for increasing the conductivity of the organic phase in a metal extraction and stripping circuit, comprising adding to the organic phase a combined formulation of one or more phenolic oxime extraction reagents, comprising one or more aldoxime extraction reagents, one or more ketoxime extraction reagents, or a combination thereof, in a water-immiscible solvent solution with an amount sufficient to create an organic phase having a conductivity of at least 250 pS/m, and more preferably, of at least 300 pS/m, as determined according to the procedures/methods of BS 5958 Part I, of at least one ketone, nitrile or amide compound, or mixture thereof, according to the instant invention. The extraction reagent, and the at least one ketone, nitrile or amide compound according to the instant invention may be added to the organic phase either as a mixture or separately.

Another aspect of the present invention applies to extraction circuits using chelating agents other than the phenolic oxime extraction reagents, namely, beta diketones, as described in U.S. Pat. No. 4,065,502 (MacKay et al); U.S. Pat. No. 4,175,012 (MacKay et al); and U.S. Pat. No. 6,107,523 (Virnig et al), or alkylated 8-hydroxyquinolines, as described in U.S. Pat. No. 3,637,711 (Budde, Jr. et al); U.S. Pat. No. 4,045,441 (Richards et al); and U.S. Pat. No. 4,066,652 (Hartlage), the contents of each of these six Patents are incorporated herein by reference. Thus, the invention further provides a method of increasing the conductivity of such a diketone or alkylated 8-hydroxyquinoline extraction reagent formulations by combining such a diketone or alkylated 8-hydroxyquinoline extraction reagent with at least one ketone, nitrile or amide compound, or mixture thereof, according to the invention. The invention still further provides a method for increasing the conductivity of an organic phase in an extraction circuit utilizing such a diketone or alkylated 8-hydroxyquinoline extraction reagent by combining at least one ketone, nitrile or amide compound with the diketone or alkylated 8-hydroxyquinoline extraction reagent in such organic phase.

Still another aspect of the present invention is the disclosure of a series of novel ketone, nitrile and amide compounds, which, when combined individually, or as mixtures of ketones, nitrites and/or amides, with one or more phenolic oxime extraction reagents or other extraction reagent(s) results in a synergistic increase in the conductivity of the formulation comprising the reagent(s) and one or more of these new compounds, and, therefore, a significant reduction of the potential of electrostatic charge buildup in the organic phases comprising those formulations in a solvent extraction circuit.

DETAILED DESCRIPTION OF THE INVENTION

Various ketones, nitrites and amides having the respective applicable structural formulas (I), (II), (III) and (IV) are new:

Formula (I)

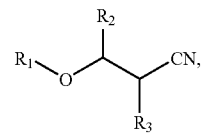

where $R_1$ is a straight- or branched-chain alkyl or alkenyl group containing 1-to-20 carbon atoms, a $C_6$-aryl group, or a $C_7$-$C_{18}$-alkylaryl group; and $R_2$ and $R_3$ are, independently, H, a straight- or branched-chain alkyl or alkenyl group containing 1-to-20 carbon atoms, a $C_6$-aryl group, or a $C_7$-$C_{18}$-alkylaryl group, such that the total number of carbon atoms between $R_2$ and $R_3$ is 9-to-30;

Formula (II)

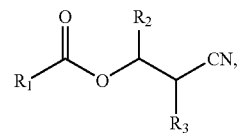

where $R_1$, $R_2$ and $R_3$ are, independently, as defined above;

Formulas (III) and (IV)

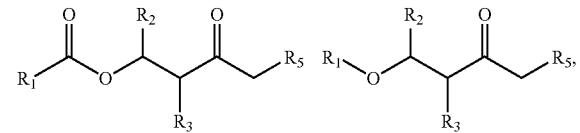

where $R_1$, $R_2$, and $R_3$ are, independently, as defined above, and $R_5$ is H, a straight- or branched-chain alkyl or alkenyl group containing 1-to-20 carbon atoms, a $C_6$-aryl group, or a $C_7$-$C_{18}$-alkylaryl group, such that the total number of carbon atoms among $R_2$, $R_3$ and $R_5$ is 9-to-30;

and not known as equilibrium modifiers or to be a part of the organic phase in a metal leaching-solvent extraction and stripping circuit in a metal refining process, have now been found to advantageously provide high electrical conductivity when formulated with phenolic oxime extraction reagents, and to be especially beneficial for use, as part of these formulations, in the organic phase in a metal solvent extraction and stripping circuit to reduce the risk of static electricity buildup in those circuits.

These compounds, which may be considered and used in a manner similar to equilibrium modifiers, may generally be formulated and used in a manner known in the art. For example, U.S. Pat. No. 4,507,268 (Kordosky et al), the contents of which are incorporated herein by reference, describes extraction reagents formulated with various oxime extractants, including hydroxyaryl aldoxime extractants, which are employed in water-insoluble, water-immiscible organic solvents, such as kerosene, with certain equilibrium modifiers, such as long-chain alkyl phenols (e.g., nonylphenol), aliphatic alcohols (e.g., tridecanol, a commercially-available branched-chain alcohol), and organophosphorous compounds (e.g., tributyl phosphate).

Kordosky et al translated the amount of modifier that would result in different net copper transfers with the particular aldoxime employed, exemplified by 2-hydroxy-5-nonylbenzaldoxime, into a measure, designated the "degree of modification" of the extraction reagent(s), which is defined as the inverse ratio of (A) the copper concentration (grams per liter copper) in an organic phase containing a set amount of extraction reagent(s), without equilibrium modifier(s), at equilibrium with an electrolyte containing a fixed concentration of copper and sulfuric acid, to (B) the copper concentration (grams per liter copper) in an organic phase containing a set amount of the same extraction reagent(s), with (a) selected equilibrium modifier(s), in an organic phase at equilibrium with the same electrolyte, under the same conditions.

Under this definition, the presence of relatively small quantities of an equilibrium modifier(s) will shift the extraction equilibrium slightly, resulting in minor diminution of reagent(s)-loaded copper concentration at equilibrium, as will be reflected by a degree of modification value closely approaching 1.0, e.g., 0.99. Increased effective quantities of modifier(s), under otherwise identical conditions, will result in a more pronounced shift in extraction equilibrium and a more pronounced diminution of copper level in the extraction reagent(s) at equilibrium, as will be reflected by a degree of modification corresponding less than 1.0. In simpler terms, the lower the degree of modification for a given extraction reagent formulation, the weaker the reagent is in terms of extractant strength and the greater the net transfer of copper. In comparing the relative extractant strengths and hydrometallurgical performance of different reagent formulations, a simplified approach is to determine the equilibrated strip point for a given formulation. Extraction reagents containing equal amounts of phenolic oxime extractants and having identical equilibrated strip points will perform essentially identically in terms of copper extraction strength and copper transfer.

This same degree of modification measure is adopted herein, as the ketone, nitrile and/or amide compounds, both novel and known, according to the invention affect both the reduction of the potential of electrostatic charge buildup in solvent extraction circuits and the equilibrium conditions of the copper extraction from the pregnant leach aqueous solutions in the circuit. It is, therefore, important that the plant operator employs the appropriate amount of the conductivity-enhancing ketone, nitrile or amide compounds, or combinations/mixtures thereof, according to the invention, in the solvent extraction circuit, as both the safety (conductivity enhancement) and the efficiency of the extraction operations may be effected.

Expectedly, the degree of modification resulting from a given combination of the ketone, nitrile and/or amide compound(s), or mixtures thereof, according to the invention with the aldoxime, ketoxime, or mixture thereof as extraction reagent(s) will vary depending on various factors. Most significantly these factors include the chemical identity and nature of the conductivity-enhancing compound used, as well as the conditions involved, such as the temperature, and such number must be empirically determined.

Many phenolic oxime extractant reagents are known in the art and would be useful in formulations with the conductivity-enhancing compounds of the instant invention. Particularly preferred phenolic oxime extractant reagents for the present invention include 2-hydroxy-5-nonylacetophenone oxime (a ketoxime), 5-nonylsalicylaldoxime (a $C_9$-aldoxime) and 5-dodecylsalicylaldoxime (a $C_{12}$-aldoxime). A further commercially-useful aldoxime is 5-octylsalicylaldoxime, and commercially-useful ketoximes would include 2-hydroxy-5-octylacetophenone oxime, 2-hydroxy-5-dodecylacetophenone oxime, 2-hydroxy-5-nonylpropriophenone oxime, 2-hydroxy-5-octylpropriophenone oxime, and 2-hydroxy-5-dodecylpropriophenone oxime.

The resulting highly-conductive extraction reagent formulations of extraction reagent(s) and ketone, nitrile, and/or amide compounds are employed in the organic phase of a metal extraction circuit in amounts of from 10%-to-50%, by volume, preferably, from 15%-to-45%, by volume, and more preferably, from 15%-to-40%, by volume, based on the volume of the combined extraction reagent formulation of extraction reagent(s) and conductivity-enhancing modifier(s) to the total volume of the organic phase, where the combined extraction reagent formulations of the invention preferably have electrical conductivities of at least 4,000 pS/m, and more preferably, of at least 8,000 pS/m, measured according to the procedures/methods of BS5958 Part I.

The following Examples, Tables and related information are intended to illustrate the invention, but not to limit it.

EXAMPLES

The composition of the various phenolic oxime extraction reagents used (all by their Cognis Corporation product name, except for the last two) in terms of their phenolic oxime components, is summarized in Table 1. Reagents having the following oxime components are of particular interest for the present invention: 2-hydroxy-5-nonylacetophenone oxime (a ketoxime), 5-nonylsalicylaldoxime (a $C_9$-aldoxime) and 5-dodecylsalicylaldoxime (a $C_{12}$-aldoxime). The oximes are formulated in a hydrocarbon diluent such as ShellSol® D70, a product of Shell Chemicals or Orfom® SX 12, a product of Chevron Phillips Chemical Company.

TABLE 1

Extraction Reagent Compositions

| Reagent Type | Name | Ketoxime Conc (m/l) | $C_9$-Aldoxime Conc (m/l) | $C_{12}$-Aldoxime Conc (m/l) |
| --- | --- | --- | --- | --- |
| Non-Modified | LIX ® 84-I | 1.5 | | |
| | LIX ® 84-IC | 2.2 | | |
| | LIX ® 860N-I | | 1.8 | |
| | LIX ® 860N-IC | | 2.5 | |
| | LIX ® 860-IC | | | 2.14 |
| | LIX ® 984N | 0.8 | 0.9 | |
| | LIX ® 984N-C | 1.1 | 1.3 | |
| | LIX ® 973NS-LV | 0.5 | 1.3 | |
| Modified | LIX ® 622N | | 1.8 | |
| | LIX ® 624N-LV | | 1.8 | |
| | LIX ® 664N-LV | | 1.8 | |
| | LIX ® 674N-LV | | 1.8 | |
| | LIX ® 6422N-LV | | 1.8 | |
| | LIX ® 612N-LV | | 1.8 | |
| | LIX ® 616N-LV | | 1.8 | |
| | Acorga ® M5640[1] | | 1.8 | |
| | Acorga ® M5774[1] | | 1.8 | |

[1] A product of Cytec Industries Inc., West Patterson, New Jersey

Table 2 below shows the conductivity, all low, of typical unmodified phenolic oxime extractants, as measured according to the methods of BS5958 Part I. A liquid sample (22 ml)

of the organic material of interest was placed in a standard test cell, to which a voltage of 5V DC was applied, and a Wolfson Electrostatics Liquid Conductivity Meter Model L30 was used for the measurements.

TABLE 2

Conductivity of Non-Modified Reagents

| Reagent | Temp (° C.) | Conductivity (pS/m) Min | Conductivity (pS/m) Max |
|---|---|---|---|
| LIX ® 84-I | 23 | 46 | 47 |
| LIX ® 84-IC | 24.6 | 58 | 59 |
| LIX ® 860N-I | 23 | 101 | 102 |
| LIX ® 860N-IC | 23 | 33 | 35 |
| LIX ® 984N-C | 24.4 | 88 | 93 |
| LIX ® 973NS-LV | 25 | 53 | — |
| LIX ® 860-IC | 23 | 23 | 23 |

In the case of the modified extraction reagents shown in the Tables below, the particular modifier is identified in the Tables, along with the equilibrated strip point, which is a measure of the level of modifier present in the formulation, where increasing the modifier content results in a lower equilibrated strip point. Reagents having identical copper max loads (oxime concentration) and equilibrated strip points give essentially-identical hydrometallurgical performance in terms of copper recovery.

Table 3 compares the conductivity of an extraction reagent containing a branched alcohol equilibrium modifier with one containing a linear alcohol equilibrium modifier. The linear alcohol equilibrium modifier provides a marginal improvement, but not sufficient to impart a true benefit, in conductivity over the branched alcohol equilibrium modifier.

TABLE 3

Alcohol-Modified $C_9$-Aldoxime

| Reagent | Modifier | Equil Strip Point (gpl Cu) | Conductivity (pS/m) at 24.5° C. Min | Conductivity (pS/m) at 24.5° C. Max |
|---|---|---|---|---|
| LIX ® 622N | Iso Tridecanol | 2.05 | 71 | 72 |
| LIX ® 624N-LV | n-Dodecanol | 1.65 | 270 | 272 |

Table 4 compares the conductivity of extraction reagents containing a linear ester equilibrium modifier with those containing a branched ester equilibrium modifier. The use of the linear esters equilibrium modifiers results in extractant formulations having a significantly higher conductivity as compared to the corresponding extraction reagents which use a branched ester as an equilibrium modifier, but still below true beneficial levels.

TABLE 4

Ester-Modified $C_9$-Aldoxime Extractant Reagents

| Reagent | Modifier | Equil Strip Point (gpl Cu) | Conductivity (pS/m) at 22-23° C. Min | Conductivity (pS/m) at 22-23° C. Max |
|---|---|---|---|---|
| LIX ® 664N-LV | di-n-butyl adipate | 1.8 | 505 | 515 |
| LIX ® 674N-LV | di-n-butyl adipate | 1.65 | 920 | 940 |
| none | ethyl octanoate | 1.8 | 1,500 | |
| Acorga ® M5640 | 2,2,4-trimethyl-1,3-pentanediol di-isobutyrate | 1.8 | 53 | 54 |
| Acorga ® M5774 | 2,2,4-trimethyl-1,3-pentanediol di-isobutyrate | 1.65 | 550 | 555 |

Table 5 shows the conductivity of extraction reagents containing a variety of different ketones as equilibrium modifiers. The ketone compounds provide significantly higher conductivity values than with either the alcohol equilibrium modifiers (Table 3) or ester equilibrium modifiers (Table 4).

TABLE 5

Ketone-Modified $C_9$-Aldoxime

| Run | Reagent | Compound | Equil Strip Point (gpl Cu) | Conductivity (pS/m)[1] Min | Conductivity (pS/m)[1] Max |
|---|---|---|---|---|---|
| 1 | LIX ® 6422N-LV | 2,6,8-trimethyl-4-nonanone | 1.8 | 14,000 | 14,000 |
| 1 | LIX ® 612N-LV | 2,6,8-trimethyl-4-nonanone | 1.65 | 11,000 | 13,000 |
| 2 | | | | 10,000 | 12000 |
| 3 | | | | 11,000 | 13,000 |
| 4 | | | | 9,000 | 12,000 |
| 1 | Non-commercial $C_9$-aldoxime | 3,3,5-trimethyl cyclohexanone | 1.65 | 8,200 | |
| 1 | LIX ® 616N-LV[2] | $C_{11}$-ketone[3] | 1.65 | 53,000 | 55,000 |
| 1 | Non-commercial $C_9$-aldoxime | 5-ethyl-2-nonanone | 1.8 | 6,900 | |
| 1 | Non-commercial $C_9$-aldoxime | 5-ethyl-2-nonanone | 1.65 | 12,000 | |

[1]Measurements made at 22-24° C.
[2]Contains 33 gpl of 2,6,8-trimethyl-4-nonanone and 240 gpl of $C_{11}$-ketone.
[3]A product of Eastman Chemical.

Table 6 shows the conductivity of extraction reagents containing nitrile, amide and ether equilibrium modifiers. All are very good modifiers. The nitrile and amide equilibrium modifiers have very high conductivities, similar to the ketone equilibrium modifiers (Table 5). The ether equilibrium modifiers are relatively weak contributors in terms of conductivity of the formulation.

TABLE 6

Other Nitriles, Amides, Ethers and Esters with $C_9$-Aldoxime

| Type | Modifier | Equil Strip Point (gpl Cu) | Conductivity (pS/m)[1] Min | Conductivity (pS/m)[1] Max |
|---|---|---|---|---|
| Nitriles | 3-cyclohexyloxyproprionitrile | 1.8 | 31,000 | 35,000 |
| | Undecylcyanide | 1.8 | 110,000 | |
| Amides | N,N-dimethyl decanoamide | 1.8 | 8,100 | |
| | | 1.65 | 13,000 | |

TABLE 6-continued

Other Nitriles, Amides, Ethers and Esters with C₉-Aldoxime

| Compound | | Equil Strip Point (gpl Cu) | Conductivity (pS/m)[1] | |
|---|---|---|---|---|
| Type | Modifier | | Min | Max |
| Ethers | Di-n-hexyl ether | 1.8 | 305 | 325 |
| Ethers | t-butyl n-octyl ether | 1.8 | 123 | 125 |
| | | 1.65 | 121 | 125 |
| | Diethylene glycol di-n-butyl ether | 1.8 | 240 | 250 |
| | | 1.65 | 345 | 355 |

[1]Measurements made at 22-23° C.

Table 7 shows the electrical conductivity of the extraction reagent LIX® 612N-LV, which contains the ketone, 2,6,8-trimethyl-4-nonanone, at various concentrations in various commercial hydrocarbon diluents (i.e., in representative organic phases). In these cases, the samples were all washed twice with fresh volumes of 150 gpl sulfuric acid and then centrifuged to remove any entrained aqueous prior to measurement. This washing was carried out to remove any trace impurities from the manufacturing process that might result in false-positive conductivity measurements. Clearly, the ketone-modified formulations give significant conductivity benefits to the resulting organic phase, even at extractant formulation concentrations as low as 10% (v/v).

TABLE 7

Effect of Diluent and Concentration on Conductivity of LIX ® 612N-LV

| Concentration | | Conductivity (pS/m) at 22-23° C. | |
|---|---|---|---|
| (% v/v) | Diluent | Min | Max |
| 5 | Chevron Phillips SX-80[1] | 23 | |
| 10 | | 185 (141) | 189 |
| 20 | | 295 | 300 |
| 30 | | 980 | 995 |
| 40 | | 1970 | 2005 |
| 10 | ShellSol ® 2046[2] | 220 | 230 |
| 20 | | 184 | 215 |
| 30 | | 505 | 510 |
| 40 | | 1480 | 1490 |
| 20 | ShellSol ® D70[2] | 250 | 255 |
| 20 | Conosol ® 170ES[3] | 134 | 135 |

[1]A product of Chevron Phillips Chemical Company.
[2]A product of Shell Chemicals.
[3]A product of Conoco Phillips Chemical Company.

Table 8 shows the significant enhancement of electrical conductivity of a representative organic phase provided by the ketone-formulated reagent, LIX® 612N-LV, over the branched ester-formulated reagent, Acorga® M 5774, having the equivalent degree of modification.

TABLE 8

Comparison of the Conductivity of LIX ® 612N-LV and M5774

| Reagent | Diluent | Concentration (% v/v) | Conductivity (pS/m) at 22-23° C. | |
|---|---|---|---|---|
| | | | Min | Max |
| LIX ® 612N-LV | ShellSol ® 2046[1] | 20 | 184 | 215 |
| | | 40 | 1480 | 1490 |

TABLE 8-continued

Comparison of the Conductivity of LIX ® 612N-LV and M5774

| Reagent | Diluent | Concentration (% v/v) | Conductivity (pS/m) at 22-23° C. | |
|---|---|---|---|---|
| | | | Min | Max |
| M5774 | ShellSol ® 2046 | 20 | 55 | |
| | | 40 | 42 | |

[1]A product of Shell Chemicals.

Table 9 shows the conductivity for two representative organic phases containing unmodified extraction reagents at two different concentrations. The ketone, nitrile or amide compounds exemplified above offer significant conductivity advantages over both the unmodified reagents (Table 9) and the extractants formulated with an ester modifier, such as TXIB (Table 8).

TABLE 9

Comparison of the Conductivities of Unmodified Reagents

| Reagents | Concentrations[2] (% v/v) | Conductivity (pS/m)[1] | |
|---|---|---|---|
| | | Min | Max |
| LIX ® 84-I | 5 | 12 | 13 |
| | 10 | 29 | 30 |
| LIX ® 984N | 20 | 270 | 290 |
| | 40 | 270 | 280 |

[1]Measurements made at 22-23° C.
[2]Diluent was SX-80, a product of Chevron Phillips Chemical Company.

The data in Table 10 shows a comparison of the conductivities of an extraction reagent-with-nitrile compound and undeclycyanide alone at various concentrations in SX-80. This footnoted data shows a significant synergistic effect between the nitrile and the extraction reagent in the combination, with the nitrile by itself contributing only a very small amount to the aggregate conductivity. When combined with the data from Table 9 and Table 2 that indicate that the C₉-aldoxime, by itself, does not contribute much to the conductivity of the formulation, it is clear that the conductivity of the combined reagent formulation-with-nitrile is significantly higher than the sum of the contributions of the nitrile and the oxime by themselves.

TABLE 10

Comparison of the Conductivities of an Organic Phase w/Reagent[1] Formulations having Various Reagent Concentrations in SX-80 and a Nitrile Compound Alone

| Reagent Conc (%(v/v)) | Organic Phase Conductivity[2] (pS/m) | Nitrile Alone Conductivity[3,4] (pS/m) |
|---|---|---|
| 10 | 79 | 3.2 |
| 20 | 480 | 45 |
| 30 | 1560 | 82 |
| 40 | 4910 | 235 |

[1]Reagent was C₉-aldoxime, modified with undecylcyanide to give an equilibrated strip point of 1.8 gpl Cu and Cu max load of 5.6 gpl. Conductivity of the formulated reagent was 142,000 pS/m at 24° C.
[2,3]Measurements of the organic phase containing the reagent formulation, and the additive alone, were carried out at 24° C.
[4]The additive was diluted to a concentration equivalent to that in the corresponding reagent sample.

What is claimed is:

1. A method of forming an extraction reagent formulation comprising: providing a substantially water-immiscible solvent; adding to said solvent one or more phenolic oxime extraction reagents and at least one additive compound selected from the group consisting of

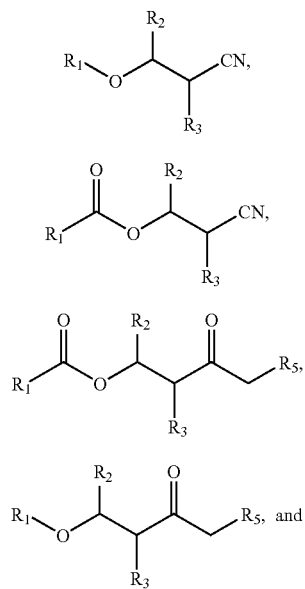

(e) combinations of two or more of these;
wherein $R_1$ is a selected from the group consisting of straight- or branched-chain alkyl or alkenyl containing 1-to-20 carbon atoms, $C_6$-aryl, and $C_7$-$C_{18}$-alkylaryl; and
$R_2$, $R_3$ and $R_5$ are independently selected from the group consisting of H, straight- or branched-chain alkyl or alkenyl containing 1-to-20 carbon atoms, a $C_6$-aryl, and $C_7$-$C_{18}$-alkylaryl, with the proviso that the total number of carbon atoms in $R_2$ and $R_3$ for (a) and (b) is about 9 to about 30; and the total number of carbon atoms in $R_2$, $R_3$ and $R_5$ for (c) and (d) is about 9 to about 30, wherein the resulting extraction reagent formulation has higher conductivity than the corresponding formulation without said additive.

2. The method according to claim 1, wherein said resulting extraction reagent formulation has a conductivity of at least 4000 pS/m, measured according to the procedures of BS 5958 Part I.

3. The method according to claim 1, wherein said additive compounds each have 8-to-30 carbon atoms and a flash point of at least 140° F.

4. The method according to claim 3, wherein said additive compounds each have 10-to-24 carbon atoms.

5. A method of increasing the conductivity of an organic phase, comprising combining, in an initial organic phase for a metal extraction circuit, one or more phenolic oxime extractant reagents and at least one additive compound selected from the group consisting of

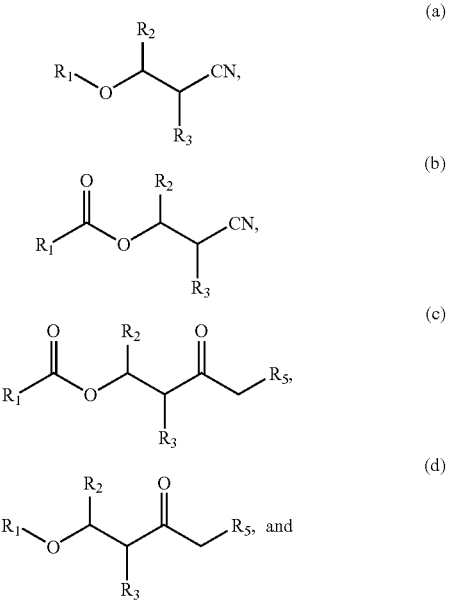

(e) mixtures thereof;
wherein $R_1$ is a selected from the group consisting of straight- or branched-chain alkyl or alkenyl containing 1-to-20 carbon atoms, $C_6$-aryl, and $C_7$-$C_{18}$-alkylaryl; and
$R_2$, $R_3$ and $R_5$ are independently selected from the group consisting of H, straight- or branched-chain alkyl or alkenyl containing 1-to-20 carbon atoms, a $C_6$-aryl, and $C_7$-$C_{18}$-alkylaryl, with the proviso that the total number of carbon atoms in $R_2$ and $R_3$ for (a) and (b) is about 9 to about 30; and the total number of carbon atoms in $R_2$, $R_3$ and $R_5$ for (c) and (d) is about 9 to about 30, wherein the resulting organic phase is more conductive than said initial organic phase.

6. The method according to claim 5, wherein said resulting organic phase has a conductivity of at least 250 pS/m, measured according to the procedures of BS 5958 Part I.

7. The method according to claim 5, wherein said resulting organic phase has a conductivity of at least 300 pS/m, measured according to the procedures of BS 5958 Part I.

8. The method according to claim 5, wherein the combination of said phenolic oxime extractant reagent(s) and said additive has a conductivity of at least 4,000 pS/m, measured according to the procedures of BS 5958 Part I.

9. The method according to claim 5, wherein said one or more phenolic oxime extraction reagents and said additive are added to organic phase in a combined mixture.

10. The method according to claim 5, wherein said one or more phenolic oxime extraction reagents and said additive are added to the organic phase separately.

11. A method of forming an extraction reagent formulation comprising: providing a substantially water-immiscible solvent; adding to said solvent at least one phenolic oxime extraction reagents and at least one additive comprising N,N-dimethyl decanoamide, wherein the resulting extraction reagent formulation has higher conductivity than the corresponding formulation without said additive.

* * * * *